(12) United States Patent
Ando et al.

(10) Patent No.: US 8,608,373 B2
(45) Date of Patent: Dec. 17, 2013

(54) SOFTENING POINT MEASURING APPARATUS AND THERMAL CONDUCTIVITY MEASURING APPARATUS

(75) Inventors: Kazunori Ando, Chiba (JP); Masayuki Iwasa, Chiba (JP); Masatsugu Shigeno, Chiba (JP); Hiroumi Momota, Chiba (JP); Kazutoshi Watanabe, Chiba (JP)

(73) Assignee: SII NanoTechnology Inc. (JP)

( * ) Notice: Subject to any disclaimer, the term of this patent is extended or adjusted under 35 U.S.C. 154(b) by 745 days.

(21) Appl. No.: 12/806,364

(22) Filed: Aug. 11, 2010

(65) Prior Publication Data
US 2011/0038392 A1 Feb. 17, 2011

(30) Foreign Application Priority Data
Aug. 12, 2009 (JP) .................. 2009-187479

(51) Int. Cl.
G01N 25/02 (2006.01)
G01N 25/18 (2006.01)

(52) U.S. Cl.
USPC .............................................. 374/16; 374/44

(58) Field of Classification Search
USPC ....................................................... 374/16, 44
See application file for complete search history.

(56) References Cited

U.S. PATENT DOCUMENTS

| 6,435,015 | B1 * | 8/2002 | Yamamoto | 73/105 |
|---|---|---|---|---|
| 6,487,515 | B1 * | 11/2002 | Ghoshal | 702/136 |
| 8,214,915 | B2 * | 7/2012 | Shigeno et al. | 850/5 |
| 2002/0088937 | A1 * | 7/2002 | Ando et al. | 250/306 |
| 2002/0110177 | A1 * | 8/2002 | Nakayama et al. | 374/44 |
| 2005/0189490 | A1 * | 9/2005 | Ando et al. | 250/310 |
| 2005/0210966 | A1 * | 9/2005 | Watanabe et al. | 73/105 |
| 2006/0219916 | A1 * | 10/2006 | Kitajima et al. | 250/311 |
| 2006/0254345 | A1 * | 11/2006 | King et al. | 73/105 |
| 2008/0224374 | A1 * | 9/2008 | Hasuda et al. | 269/71 |
| 2009/0134025 | A1 | 5/2009 | Shtein et al. | 204/407 |
| 2009/0255016 | A1 * | 10/2009 | Wakiyama et al. | 850/33 |
| 2010/0058499 | A1 * | 3/2010 | Shigeno | 850/21 |
| 2010/0107284 | A1 * | 4/2010 | Shigeno et al. | 850/5 |

FOREIGN PATENT DOCUMENTS

| JP | 07146265 | 6/1995 | | |
|---|---|---|---|---|
| JP | 07325092 | 12/1995 | | |
| JP | 10253641 | 9/1998 | | |
| JP | 2004347497 A | * 12/2004 | | G01N 13/10 |
| JP | 2005283188 A | * 10/2005 | | G01N 13/10 |
| JP | 2006118966 | 5/2006 | | |
| JP | 3141861 | 5/2008 | | |
| WO | 97 40369 | 10/1997 | | |

OTHER PUBLICATIONS

Patent Abstracts of Japan, publication No. 07-325092, publication date Dec. 12, 1995.
Abstract, publication No. WO 97/40369, publication date Oct. 30, 1997.
M. Hinz et al., "High resolution vacuum scanning thermal microscopy of HfO$_2$ and SiO$_2$", Appl. Phys. Lett. 92 (2008), pp. 8/10-10/10.

* cited by examiner

*Primary Examiner* — Lisa Caputo
*Assistant Examiner* — Jamel Williams
(74) *Attorney, Agent, or Firm* — Adams & Wilks

(57) ABSTRACT

In a local softening point measuring apparatus and thermal conductivity measuring apparatus using a probe microscope as a base, environment of the prob~ and a sample surface is set to 1/100 atmospheric pressure (103 Pa) or lower. Otherwise, a side surface of the probe is coated with a thermal insulation material having a thickness that enables thermal dissipation to be reduced to 1/100 or lower, to thereby reduce the thermal dissipation from the side surface of the probe, and exchange heat substantially only at the contacting portion between the probe and the sample surface.

12 Claims, 21 Drawing Sheets

F I G. 7
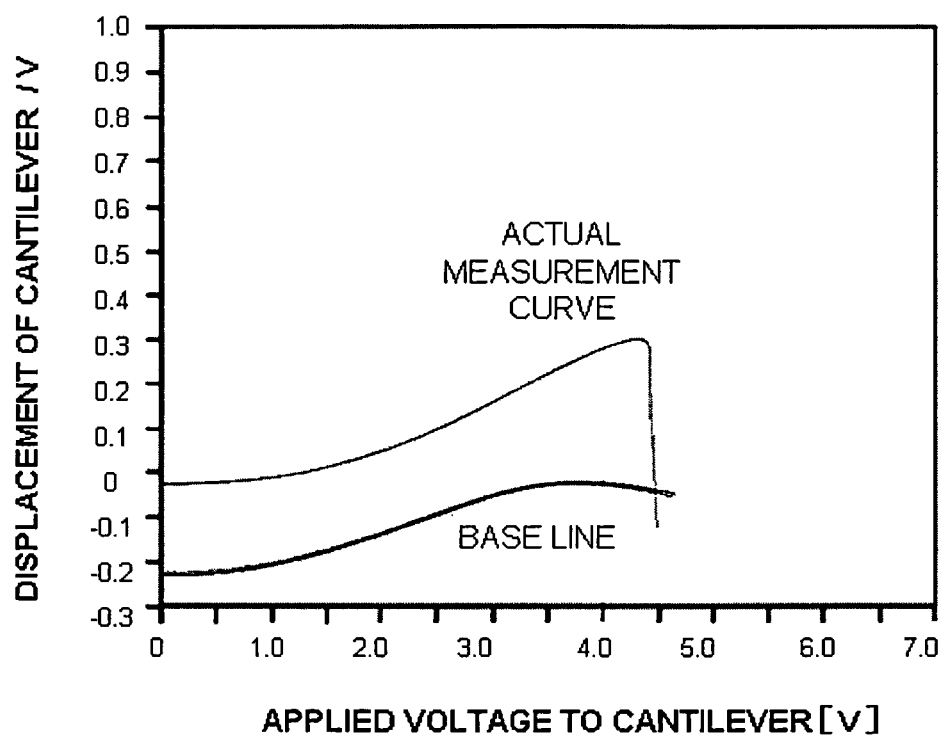

SOFTENING POINT MEASURING APPARATUS AND THERMAL CONDUCTIVITY MEASURING APPARATUS

BACKGROUND OF THE INVENTION

1. Field of the Invention

The present invention relates to a softening point measuring apparatus using a scanning probe microscope as a base, for measuring a softening point (glass transition or melting point) of a sample by detecting a flection amount of a cantilever when a contacting portion with the sample is locally heated using a heat generating portion provided to the cantilever. In addition, the present invention relates to a thermal conductivity measuring apparatus using a scanning probe microscope as a base, for measuring thermal conduction of a sample surface via the contacting portion with the sample by detecting temperature variation of the cantilever from a change in resistance of the heat generating portion of the cantilever.

2. Description of the Related Art

A conventional apparatus for measuring a softening point such as glass transition or melting point of a sample by locally heating a sample surface includes a probe having a heat generating portion, a function of heating the heat generating portion, a light source which projects light to a mirror for detecting a position provided to the probe, a detector which detects reflected light that is projected from the light source and reflected by the mirror so as to convert the same into an electric signal, and a circuit which uses an output signal of the detector as a flection displacement signal of the probe. The probe tip is brought into contact with the sample surface, and the heat generating portion is heated, so that the contacting portion with the sample surface is heated. When the temperature becomes the softening point such as glass transition or melting point in accordance with the material of the sample, the probe sinks in the sample surface. This is detected as a flection displacement signal of the probe so that the softening point is measured (Japanese Patent Translation Publication No. Hei 11-509003).

In addition, a conventional apparatus for measuring thermal conduction of a sample includes a probe having a heat generating portion, a function of measuring a resistance of the heat generating portion, a light source which projects light to a mirror provided to the probe, a detector which detects reflected light that is projected from the light source and reflected by the mirror so as to convert the same into an electric signal, and a circuit which uses an output signal of the detector as a flection displacement signal of the probe. The heat generating portion of the probe is heated, a resistance value is detected, and the probe tip is brought into contact with a sample surface so as to scan the sample surface. Then, thermal flow from the probe to the sample changes in accordance with thermal conduction distribution in the sample surface so that temperature of the heat generating portion changes, which results in a variation of the resistance. Therefore, by detecting the resistance, thermal conduction distribution or the like in the sample surface may be measured (Japanese Patent Translation Publication No. Hei 11-509003).

In addition, a platinum wire or the like is used as the probe. A diameter of the wire is 6 µm and a probe tip has a tip curvature radius of 5 µm, which are too thick to realize nanometer order resolution. Instead of a manual process using the platinum wire or the like, a semiconductor process has been developed for manufacturing a cantilever made of silicon as a substitution of the wire probe.

Therefore, there are increasing cases where a cantilever made of silicon is used for a purpose of local heating, local thermal conduction measurement, or the like.

There is manufactured a cantilever made of silicon for local heating, in which heat generating portion is a doped resistor. A doped portion is made to generate heat so as to heat the sample surface locally, and a softening point of the sample is measured. There is manufactured a cantilever having a probe tip sharpened by etching of a semiconductor process (US Patent No. 20,060,254,345).

In addition, a cantilever made of silicon for measuring thermal conduction has a patterned wiring of metal thin film formed on the cantilever tip. The cantilever is heated at a constant temperature and is brought into contact with the sample surface by the probe which was comprised on the cantilever tip so as to scan the same. Then, a degree of thermal flow into the sample surface is detected as a resistance variation of the metal thin film pattern so that thermal conduction distribution or the like is measured. The cantilever of the metal thin film pattern is also manufactured by the semiconductor process (Japanese Patent Application Laid-Open No. Hei 07-325092).

The cantilever made of silicon is manufactured by the semiconductor process, and the probe tip is sharpened to be of 10 nmR or the like. The cantilever made of silicon is manufactured for heating locally or measuring local thermal conduction and is being used also in nanotechnology fields for thermal analysis.

However, it was found that even if the probe tip of the cantilever made of silicon is sharpened to be of approximately 10 nmR by the semiconductor process, measuring of the softening point or the local thermal conduction is difficult by locally heating the sample.

When the local heating is performed, the heat generating portion is heated so that the contacting portion with the sample is heated by thermal conduction to the probe. The probe tip has a curvature radius of 10 nmR, and the side surface of the probe has a pyramidal shape so as to form a surface. Therefore, the side surface of the probe is also heated, and heat of the heat generating portion is conducted from the probe to the sample contacting portion and is also dissipated via air from the side surface of the probe. Thus, it is found that the heat also affects the periphery of the probe contacting portion.

In the measurement of a softening point, if it is desired to compare characteristics of neighboring measurement points, heating operation at a first measurement point gives thermal history to the sample surface at the peripheral portion, and at the next measurement point, measurement of the softening point is performed after being affected by the thermal history, so that correct comparison of physical properties may not be performed. If the heat diffusion via air is taken into account, thermal influence by the heated probe causes substantially the same effect as that of a thicker probe despite of the sharpened probe tip.

In addition, when the thermal conduction is measured, the sample surface is scanned by the probe while detecting the resistance of the heated heat generating portion. The detection range of the resistance is not limited to the contacting portion between the probe and the sample surface but covers the range that is affected by the thermal influence due to the above-mentioned thermal dissipation from the side surface of the probe. Therefore, the thermal conduction may not be measured correctly. In addition, it was found that if the sample surface has a level difference, thermal dissipation occurs in the same manner as described above when the side surface portion of the probe becomes close to the uneven part due to the level difference, and therefore thermal conduction thereof becomes different apparently despite that the surface is uniform in material, so that the thermal conduction distribution may not be measured correctly.

SUMMARY OF THE INVENTION

Therefore, it is an object of the present invention to provide a method and an apparatus for measuring a softening point by using a cantilever having a probe and a heat generating portion so as to heat a sample locally without affecting thermally a peripheral portion except a measurement point of the sample. In addition, it is another object of the present invention to provide a method and an apparatus for measuring thermal conduction in which a probe and a heat generating portion is provided, a resistance variation of the heat generating portion is measured, and heat dissipation except at a contacting portion with the sample is eliminated, to thereby correctly measure the thermal conduction only at the contacting portion. In addition, it is still another object of the present invention to provide a high sensitive apparatus in which without limiting to local heating or measurement of local thermal conduction, heat exchange is performed only at the contacting portion between the probe and a sample surface, with high resolution in a planar direction and being hardly affected by a shape such as unevenness in a perpendicular direction.

In order to solve the above-mentioned problem, the present invention provides the following units.

According to the present invention, concerning local heating, a softening point measuring apparatus using a scanning probe microscope, for measuring a softening point of a sample includes a cantilever including a probe at a tip thereof and a heat generating portion, a voltage applying unit for applying a voltage to the heat generating portion, a displacement detection unit for detecting a displacement of the cantilever, and a sample moving unit for moving the sample. The heat generating portion is heated for heating the probe so as to heat a contacting portion with the sample locally for detecting a flection amount of the cantilever so as to measure the softening point. An apparatus structure is adopted in which thermal dissipation from a side surface of the probe does not occur, and hence heat is exchanged only at the contacting portion between the probe and the sample surface. With this structure, heat does not affect a part other than the local part to be measured, and hence local heating with high sensitivity may be performed.

In addition, concerning local thermal conduction measurement, a thermal conductivity measuring apparatus using a scanning probe microscope, for measuring thermal conduction of a sample surface includes a cantilever including a probe at a tip thereof and a heat generating portion, a voltage applying unit for applying a voltage to the heat generating portion, a current detection unit of the heat generating portion, a displacement detection unit for detecting a displacement of the cantilever, and a sample moving unit for moving a sample. A resistance variation in the heat generating portion is measured so as to detect a temperature variation of the cantilever as a variation of a resistance value, to thereby measure the thermal conduction of the sample surface via a contacting portion with the sample. An apparatus structure is adopted in which thermal dissipation from a side surface of the probe does not occur, and hence heat is exchanged only at the contacting portion between the probe and the sample surface. With this structure, heat does not affect a part other than the local part to be measured, and hence local thermal conduction ratio may be measured with high sensitivity.

Concerning the above-mentioned local heating and local thermal conduction measurement, one of specific structures in which thermal dissipation from the side surface of the probe does not occur is a structure including the above-mentioned basic scanning probe microscope plus a vacuum chamber and a vacuum pumping unit so that a degree of vacuum in the environment where the probe and the sample surface are disposed is increased, to thereby eliminate a medium transferring heat. Thus, the thermal dissipation from the side surface of the probe is eliminated so that heat is exchanged only at the contacting portion between the probe and the sample surface. The degree of vacuum is preferably $1/100$ atmospheric pressure ($10^3$ Pa) or lower, which may reduce the thermal dissipation from the side surface of the probe to lower than 1%, and hence the heat exchange performed only at the contacting portion between the probe and the sample surface becomes 99% or higher.

In addition, another structure in the same manner is to cover the side surface of the probe with a thermal insulation material. In particular, $SiO_2$ and $Si_3N_4$ may be used as a material of thermal insulation coating film in the semiconductor process. By controlling the thickness of the film, thermal dissipation from the side surface of the probe of the present invention may be reduced to lower than 1%, and hence the heat exchange performed only at the contacting portion between the probe and the sample surface becomes 99% or higher.

According to the present invention, in the local heating, by reducing the thermal dissipation from the side surface of the probe, thermal exchange may be performed only at the contacting portion between the probe and the sample surface. Thus, thermal transfer to the periphery of the measurement point may be suppressed, and hence heat influence between measuring points may be eliminated and that a softening point measurement of measurement points that are close to each other by submicron order may be performed.

In addition, also in the thermal conduction measurement, heat exchange is performed only at the contacting portion between the probe and the sample surface, and hence thermal dissipation from the side surface of the probe via the air is reduced as much as possible. As a result, noise in the physical properties signal obtained by the measurement may be reduced to lower than 1%. Thus, influence of the shape corresponding to unevenness of the sample surface may be avoided, and hence measurement accuracy of the thermal conduction is improved.

BRIEF DESCRIPTION OF THE DRAWINGS

In the accompanying drawings:

FIGS. 4A to 4C illustrate an early stage of heating, a thermal expansion stage during heating, and a softening stage, respectively;

Figure 8A:
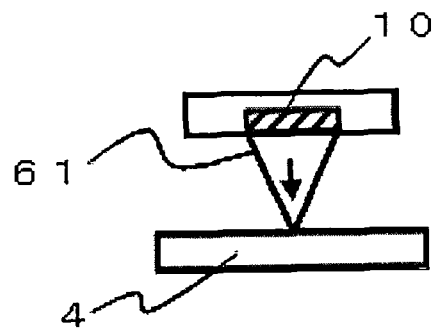
Figure 8B:
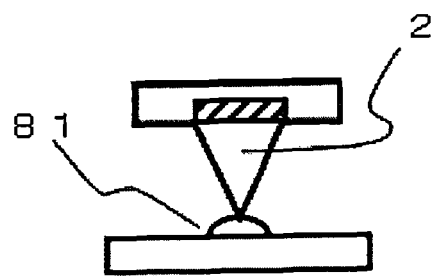
Figure 8C:
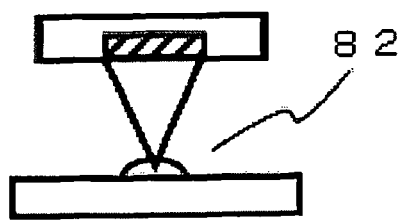
Figure 9A:
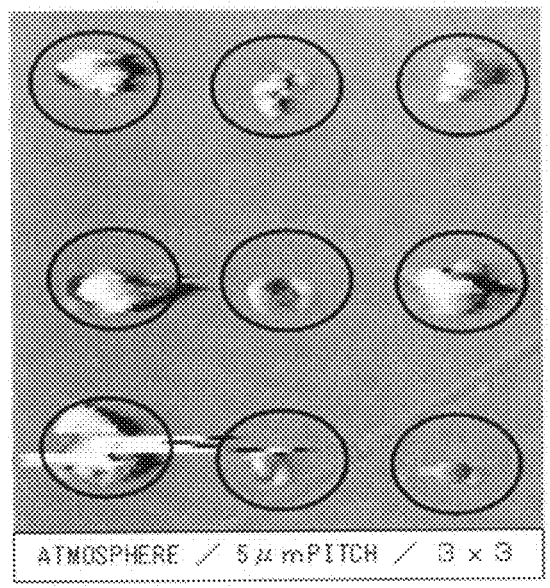
Figure 9B:
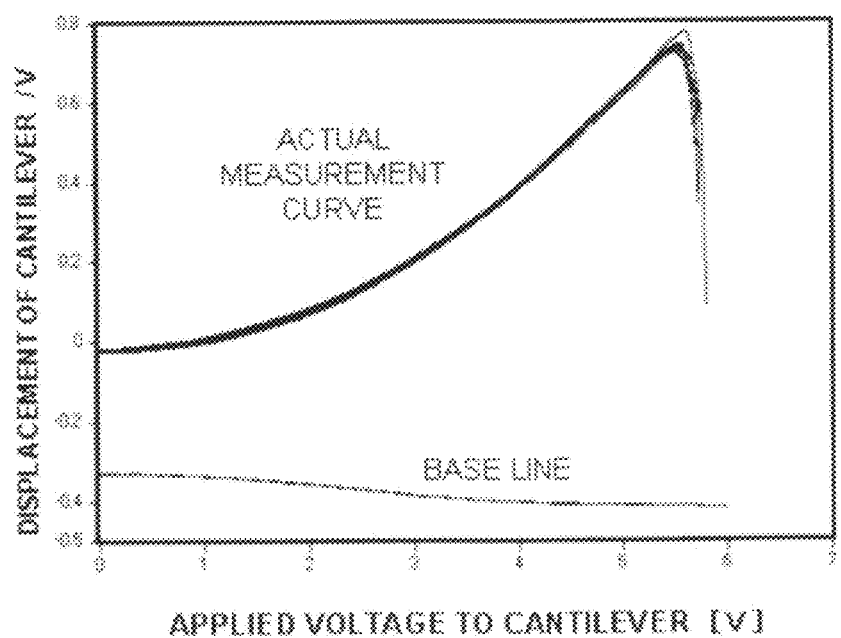
Figure 9C:
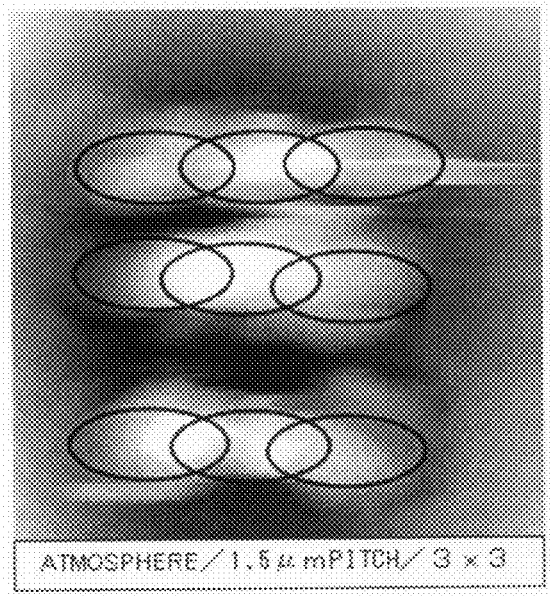
Figure 9D:
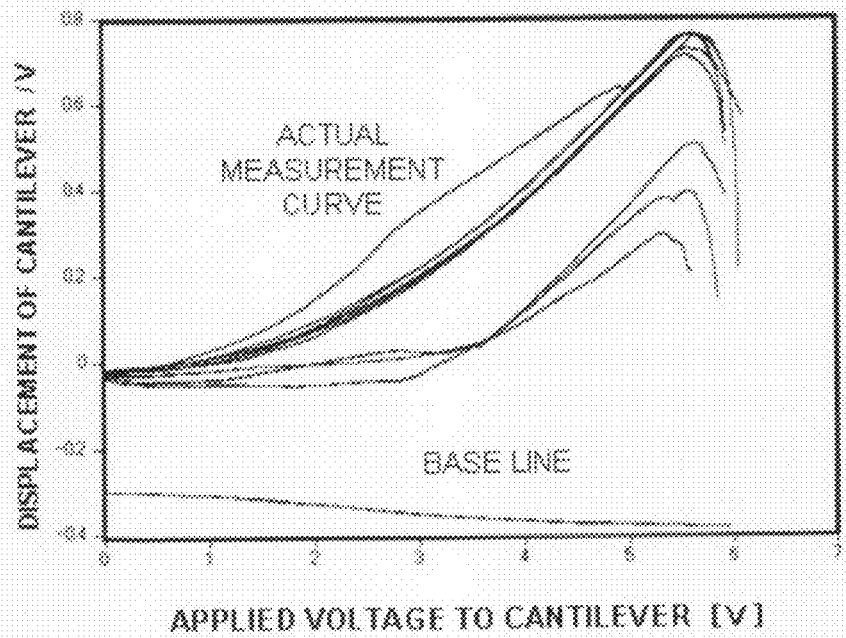
Figure 10A:
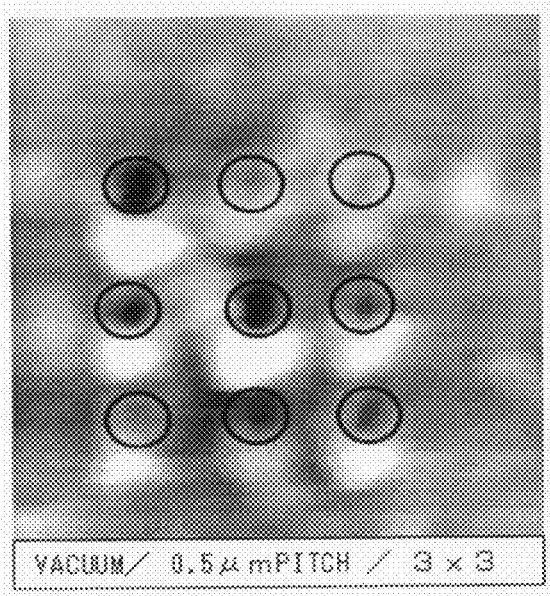
Figure 10B:
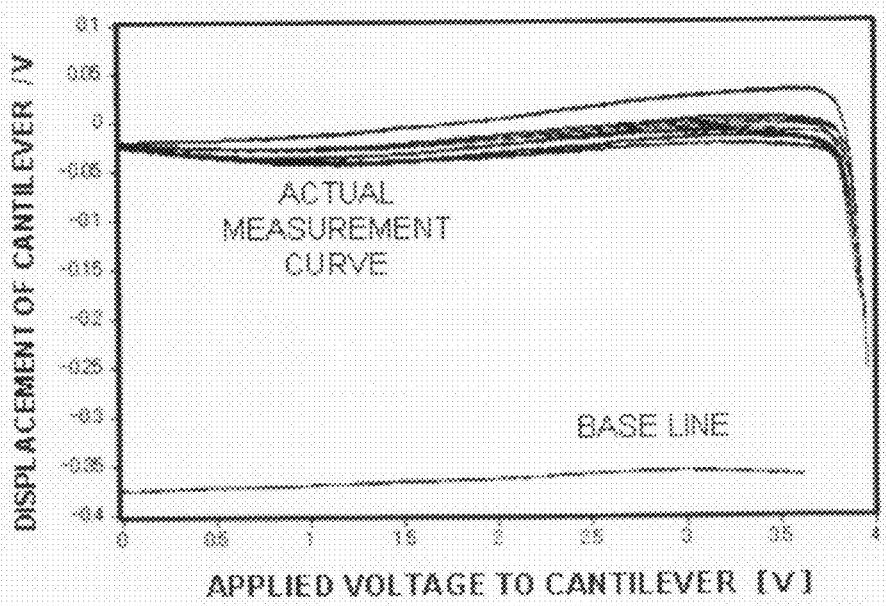
Figure 11:
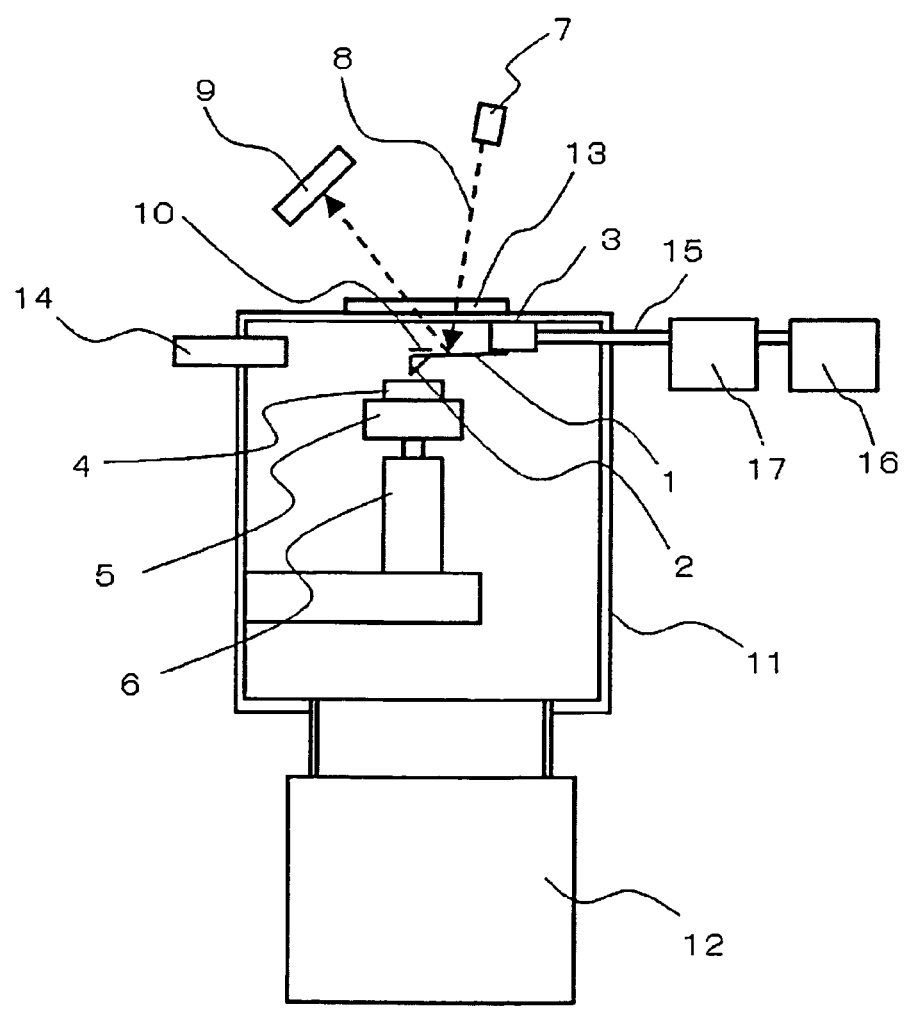
Figure 12A:
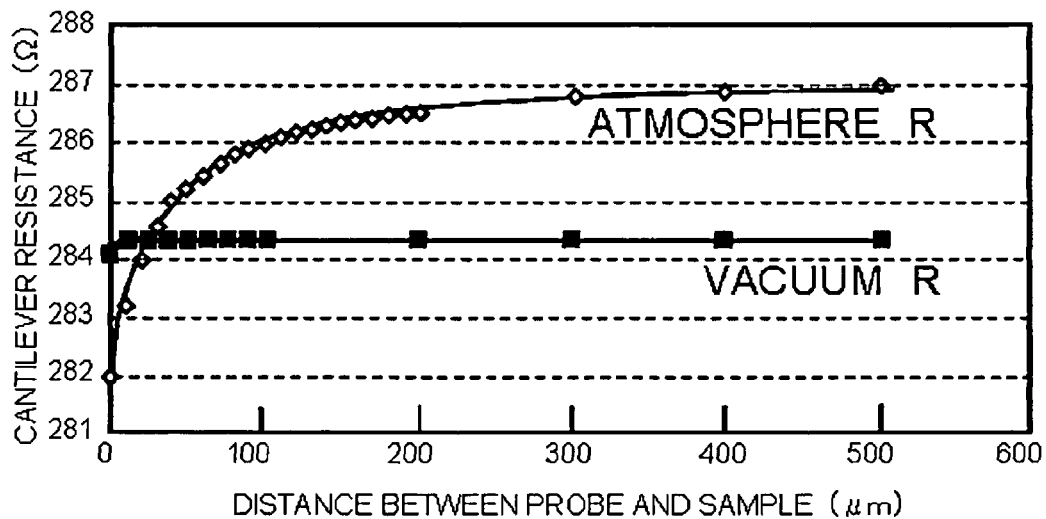
Figure 12B:
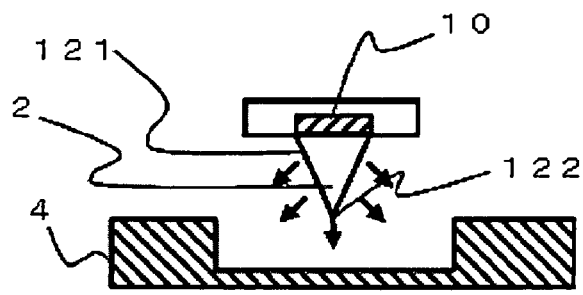
Figure 12C:
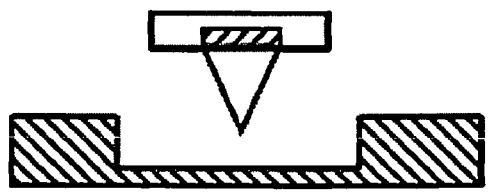
Figure 12D:
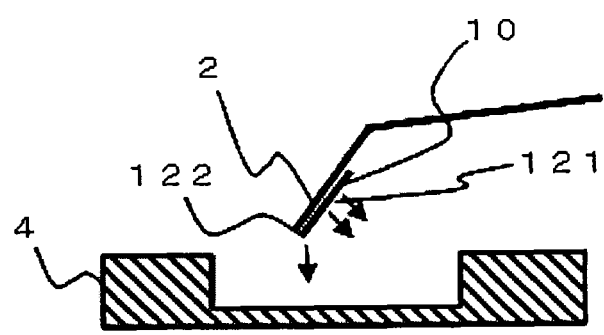
Figure 12E:
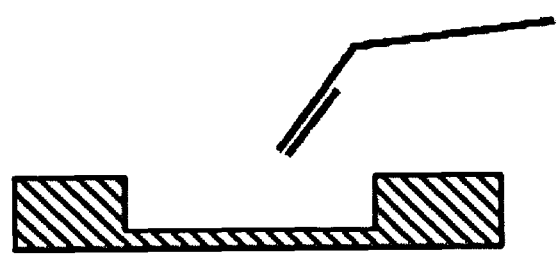
Figure 13A:
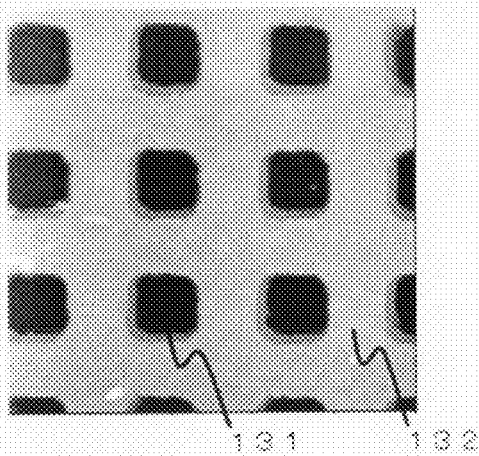
Figure 13B:
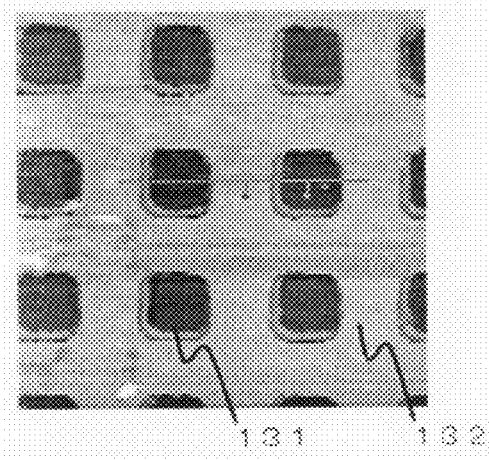
Figure 13C:
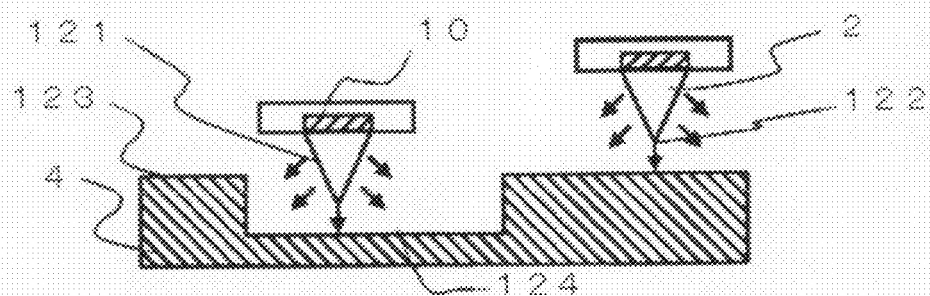
Figure 14A:
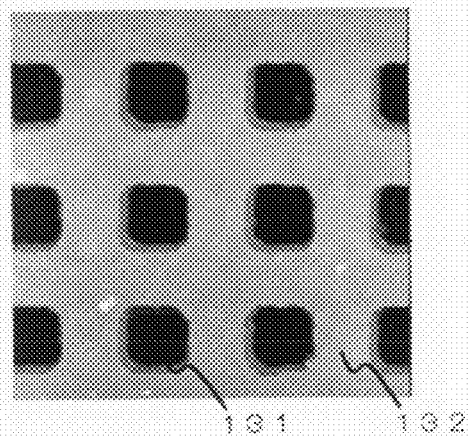
Figure 14B:
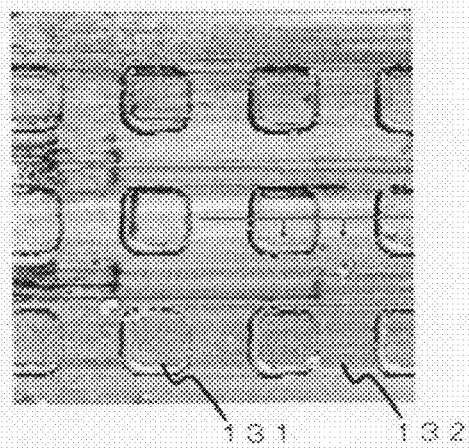
Figure 14C:
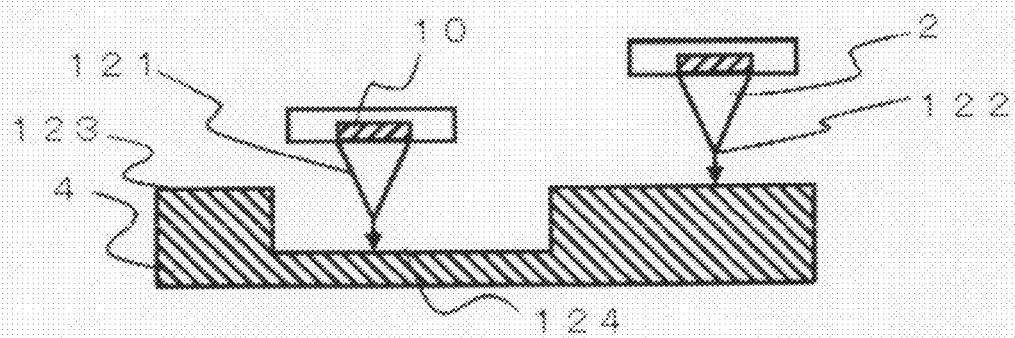
Figure 15A:
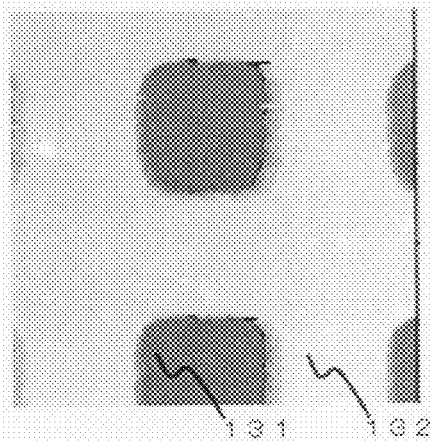
Figure 15B:
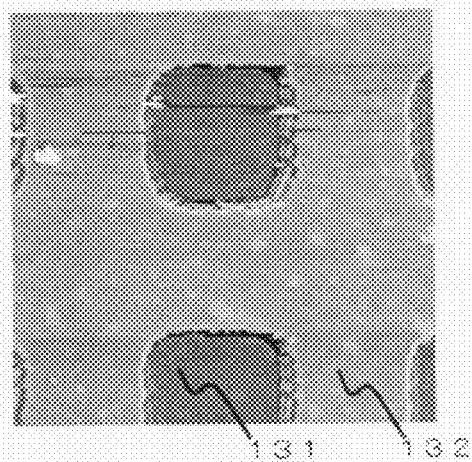
Figure 15C:
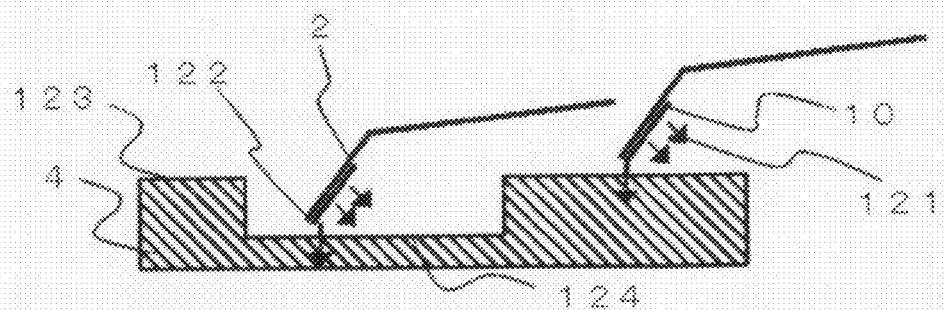
Figure 16A:
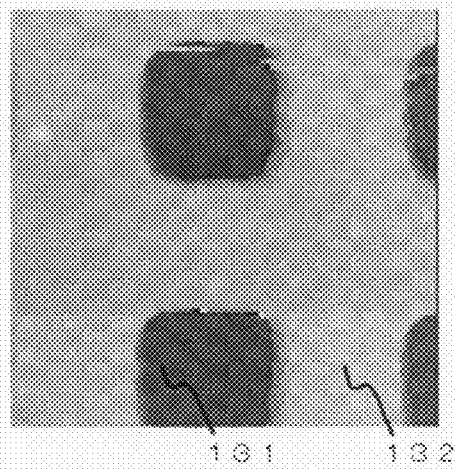
Figure 16B:
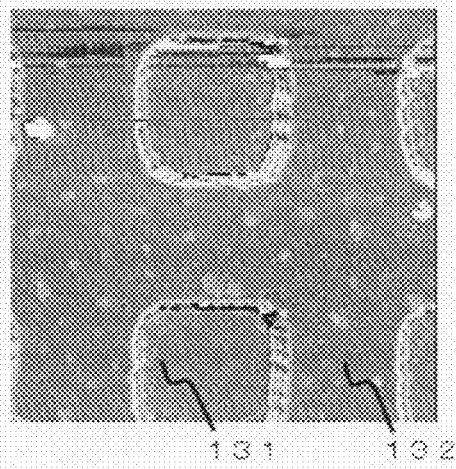
Figure 16C:
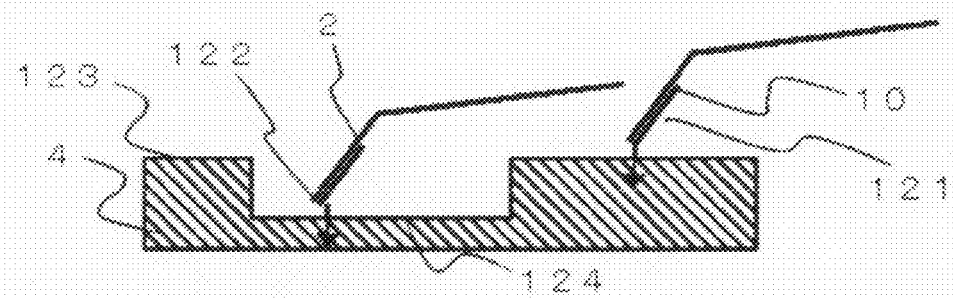
Figure 17A:
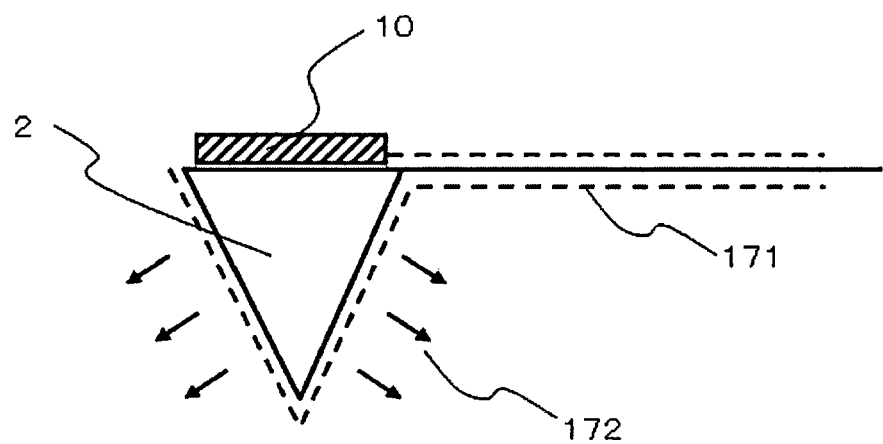
Figure 17B:
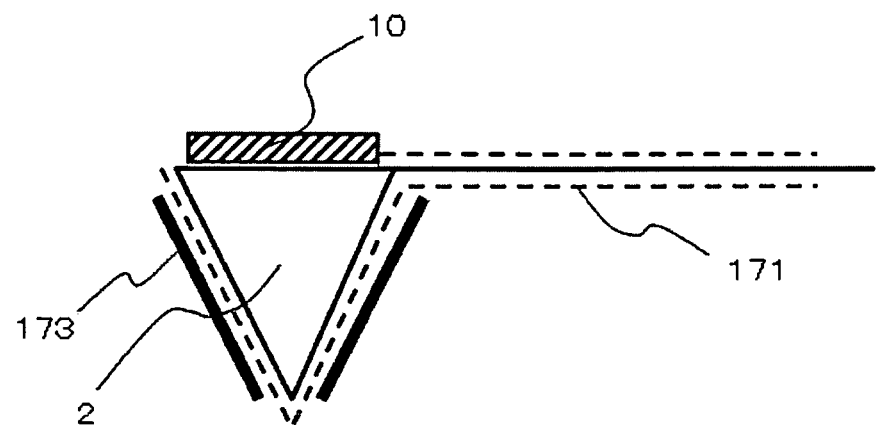
Figure 18A:
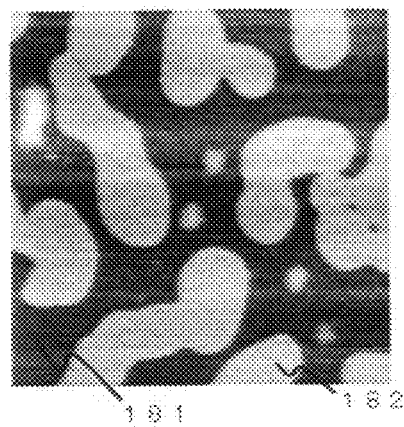
Figure 18B:
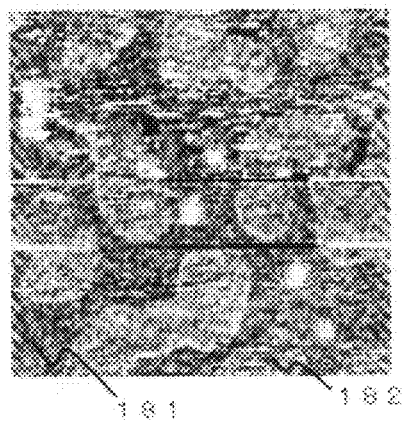
Figure 18C:
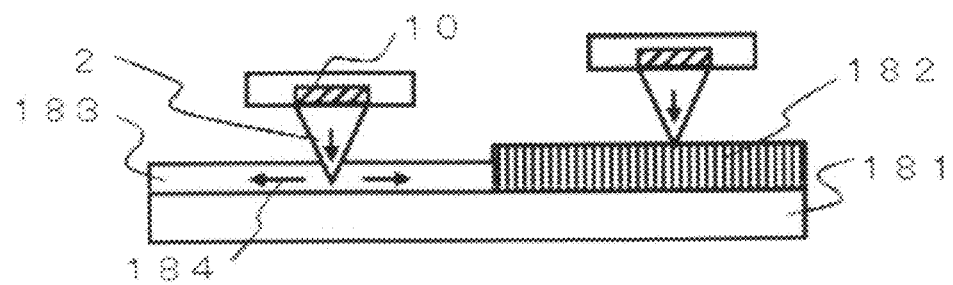
Figure 19A:
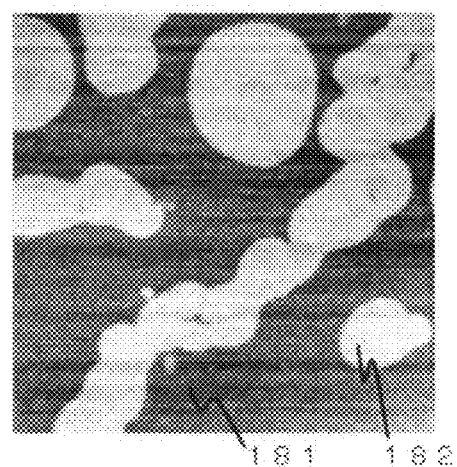
Figure 19B:
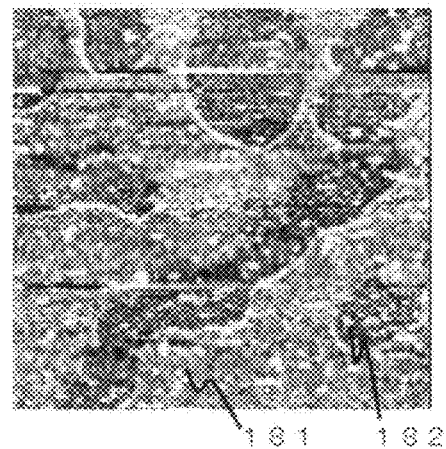
Figure 19C:
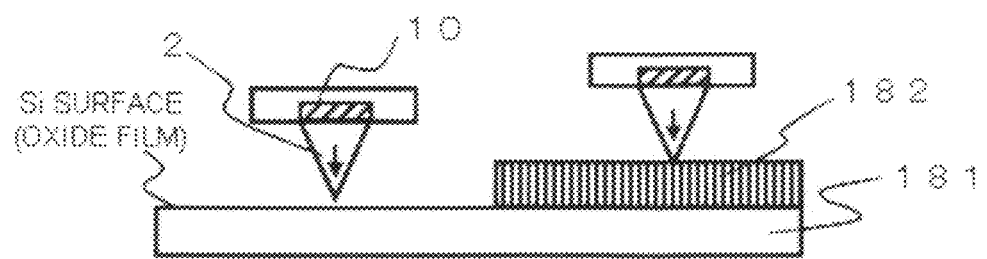
Figure 20:
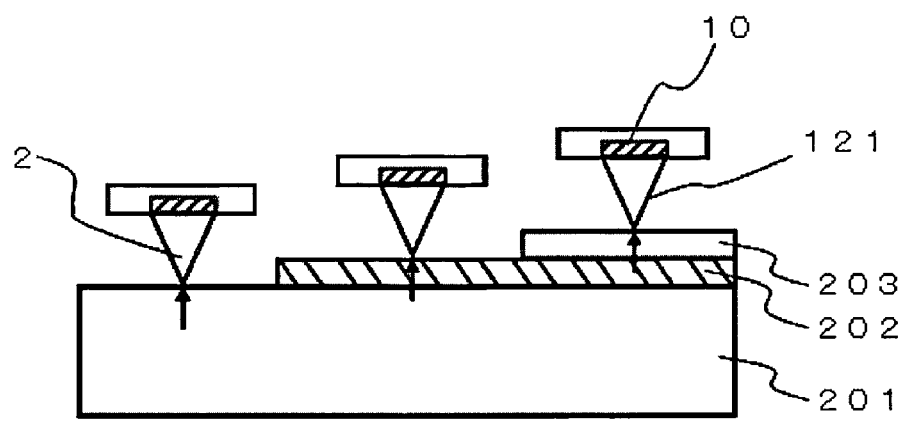

6A to 6C illustrate an early stage of heating, a thermal expansion stage during heating, and a softening stage, respectively;

FIG. 7 illustrates a result of actual measurement of a softening curve in the vacuum according to the present invention;

FIGS. 8A to 8C are explanatory diagrams of thermal flow between the probe and the sample in the vacuum according to the present invention, and FIGS. 8A to 8C illustrate an early stage of heating, a thermal expansion stage during heating, and a softening stage, respectively;

FIGS. 9A to 9D show examples of actual measurement of local heating in the atmosphere. FIG. 9A shows a surface shape image after local heating at nine points with 5 μm pitch, FIG. 9B illustrates actual measurement curves of the softening curves at the nine points, FIG. 9C shows the surface shape image after local heating at nine points with 1.5 μm pitch, and FIG. 9D illustrates an actual measurement result of actual measurement curves of softening curves at the nine points;

FIGS. 10A and 10B show examples of actual measurement of local heating in the vacuum according to the present invention. FIG. 10A shows a surface shape image after local heating at nine points with 0.5 μm pitch, and FIG. 10B illustrates an actual measurement result of actual measurement curves of softening curves at the nine points;

FIG. 11 illustrates a general structure of a thermal conductivity measuring apparatus using a scanning probe microscope according to Embodiment 2 of the present invention;

FIGS. 12A to 12E illustrate an actual measurement example of comparison between a resistance variation of a heat generating portion of a cantilever in the atmosphere and the same in the vacuum. FIG. 12A illustrates comparison curves of a dependency on a distance between the probe and the sample in the atmosphere and in the vacuum, FIG. 12B illustrates thermal dissipation in the atmosphere, FIG. 12C illustrates that there is no thermal dissipation in the vacuum, FIG. 12D illustrates thermal dissipation of another type of cantilever in the atmosphere, and FIG. 12E illustrates that there is no thermal dissipation of the another type of cantilever in the vacuum;

FIGS. 13A to 13C show an actual measurement example of a thermal conduction image when an uneven sample is measured in the atmosphere. FIG. 13A shows a surface shape image, FIG. 13B shows a thermal conduction image, and FIG. 13C illustrates thermal dissipation;

FIGS. 14A to 14C show an actual measurement example of a thermal conduction image when an uneven sample is measured in the vacuum according to the present invention. FIG. 14A shows a surface shape image, FIG. 14B shows a thermal conduction image, and FIG. 14C illustrates thermal dissipation;

FIGS. 15A to 15C show an actual measurement example of a thermal conduction image when an uneven sample is measured with another type of cantilever in the atmosphere. FIG. 15A shows a surface shape image, FIG. 15B shows a thermal conduction image, and FIG. 15C illustrates thermal dissipation;

FIGS. 16A to 16C show an actual measurement example of a thermal conduction image when an uneven sample is measured with the another type of cantilever in the vacuum. FIG. 16A shows a surface shape image, FIG. 16B shows a thermal conduction image, and FIG. 16C illustrates thermal dissipation;

FIGS. 17A and 17B are explanatory diagrams of thermal insulation coating on a side surface of the probe according to the present invention. FIG. 17A illustrates a state before thermal insulation coating, and FIG. 17B illustrates a state after thermal insulation coating;

FIGS. 18A to 18C show an actual measurement example of a thermal conduction image when a thin film sample is measured in the atmosphere. FIG. 18A shows a surface shape image, FIG. 18B shows a thermal conduction image, and FIG. 18C illustrates thermal dissipation;

FIGS. 19A to 19C show an actual measurement example of a thermal conduction image when a thin film sample is measured in the vacuum according to the present invention. FIG. 19A shows a surface shape image, FIG. 19B shows a thermal conduction image, and FIG. 19C illustrates thermal dissipation; and FIG. 20 is an explanatory diagram of thermal conduction measurement of a thin film sample in the vacuum according to the present invention.

DETAILED DESCRIPTION OF THE PREFERRED EMBODIMENTS

Hereinafter, a basic structure and a measurement principle of a softening point measuring apparatus and a thermal conductivity measuring apparatus using a scanning probe microscope according to the present invention are described with reference to the attached drawings. Note that, the drawings mainly illustrate a structure necessary for describing the present invention, and that a part of elements of the scanning probe microscope that is not relevant to embodiments of the present invention is omitted.

According to the present invention, a softening point measuring apparatus using a scanning probe microscope as a base includes: a cantilever including a probe at a tip thereof and a heat generating portion; a voltage applying unit for applying a voltage to the heat generating portion; a displacement detection unit for detecting a displacement of the cantilever; a sample moving unit for moving a sample; a vacuum chamber; and a vacuum pumping unit, in which: the heat generating portion is heated for heating the probe so as to heat a contacting portion with the sample locally for detecting a flection amount of the cantilever so as to measure a softening point of the sample; and an environment of the probe and the sample is desirably 1/100 atmospheric pressure ($10^3$ Pa) or lower. In this manner, thermal dissipation from a side surface of the probe may be reduced to be lower than 1%, and hence heat exchange performed only at the contacting portion between the probe and a sample surface becomes 99% or higher.

In addition, the side surface of the probe of the cantilever to be used is covered with a thermal insulation material so that thermal dissipation from the side surface of the probe is prevented. By this method too, the same effect may be obtained as the above-mentioned case where degree of vacuum is increased.

Hereinafter, each structure is described specifically with reference to the attached drawings.

[Embodiment 1]

Figure 1:
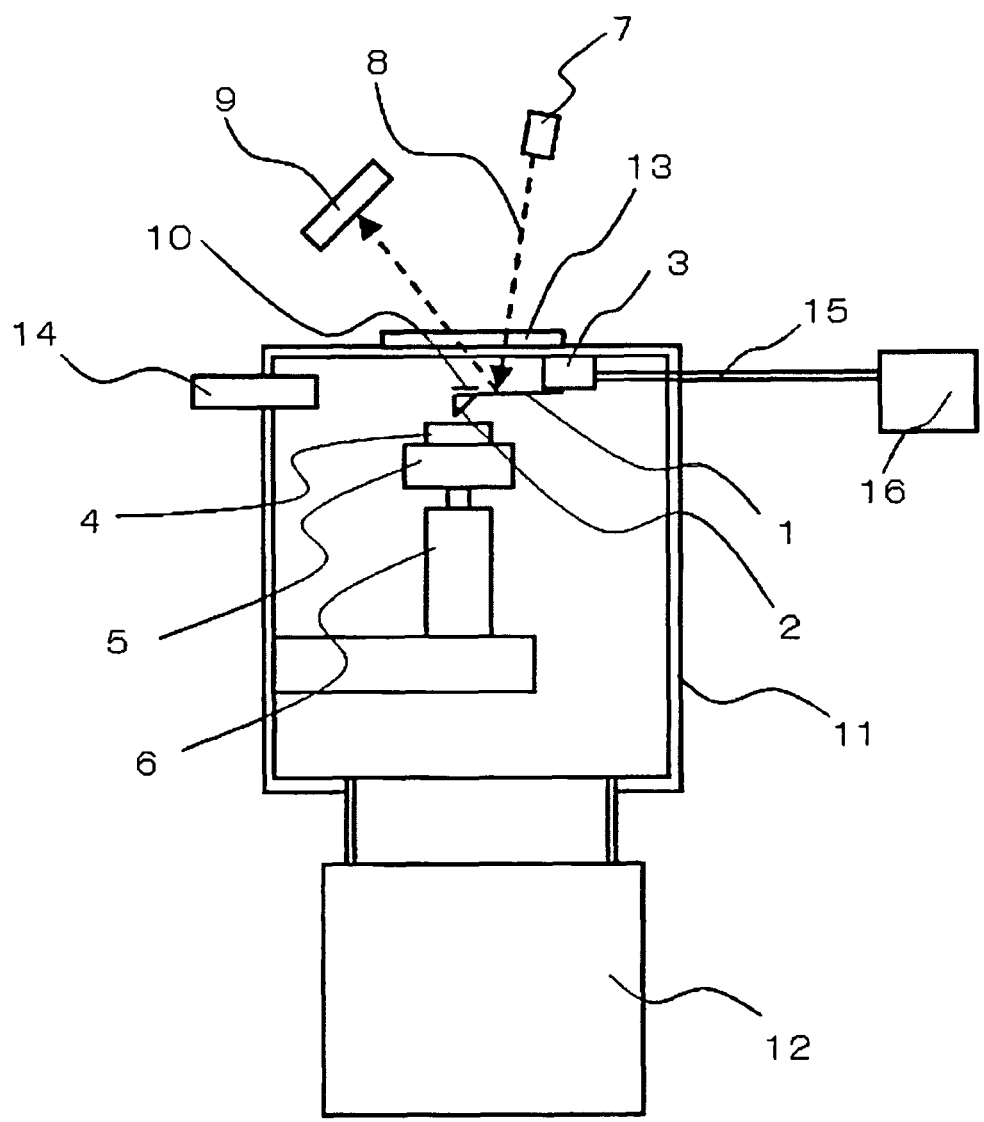
FIG. 1 illustrates a general structure of a softening point measuring apparatus using a scanning probe microscope according to Embodiment 1 of the present invention.

Embodiment 1 of the present invention is described with reference to the attached drawings. FIG. 1 illustrates a general structure of a softening point measuring apparatus using a scanning probe microscope. A cantilever 1 has a probe 2 and a heat generating portion 10 at a tip thereof and is attached to a cantilever mount 3. A sample 4 is placed on a sample table 5, and the sample table 5 is disposed on a sample moving unit 6. The sample moving unit 6 may move in a vertical direction and may move in a planar (horizontal) direction. When the sample moving unit 6 moves in the vertical direction, the probe 2 is pressed to a sample surface or is separated from the same. In the movement in the planar direction, a contact position between the probe 2 and the sample surface is moved in a relative manner, thereby enabling to scan the sample surface. The sample moving unit 6 is disposed in a vacuum chamber 11. An upper portion of the vacuum chamber 11 is provided with a transparent window 13, and vacuum sealing property is secured so that an inside of the vacuum chamber may be vacuumed by a vacuum pumping unit 12. The degree of vacuum may be checked by a vacuum gage 14. A laser light source 7 is disposed outside the vacuum chamber, and a laser beam 8 passes through the window 13 and irradiates the cantilever 1. Then, reflected light of the laser beam 8 passes through the window 13 and reaches a displacement detection unit 9. A displacement amount of the probe 2 in the vertical direction is detected as a reaching position of the light on the displacement detection unit 9. In addition, current lead wires 15 are led in the vacuum chamber 11 in a state where the vacuum sealing property and electric insulation are secured. A voltage applying unit 16 applies voltage to the heat generating portion 10 of the cantilever 1 so as to supply current for heating the probe 2. Next, an example of the cantilever having the heat generating portion is described with reference to FIGS. 2 and 3.

Figure 2:
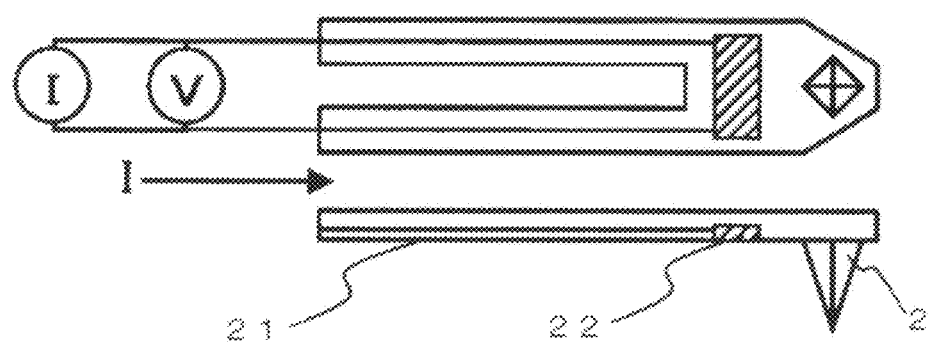
FIG. 2 illustrates an example of a cantilever that is a type in which a heat generating portion is a doped resistor.

In FIG. 2, a cantilever arm portion 21 has a slit shape, and only a part of the probe 2 is a doped resistor heat generating portion 22. The doped resistor heat generating portion 22 is a low dope region having a high resistance electrically, while the cantilever arm portion 21 is a high dope region having a low resistance electrically. Therefore, when current flows from one side of the cantilever arm portion through the doped resistor heat generating portion 22 to the other side of the cantilever arm portion, the doped resistor heat generating portion is heated. The probe 2 is heated by the doped resistor heat generating portion 22 via thermal conduction.

Figure 3:
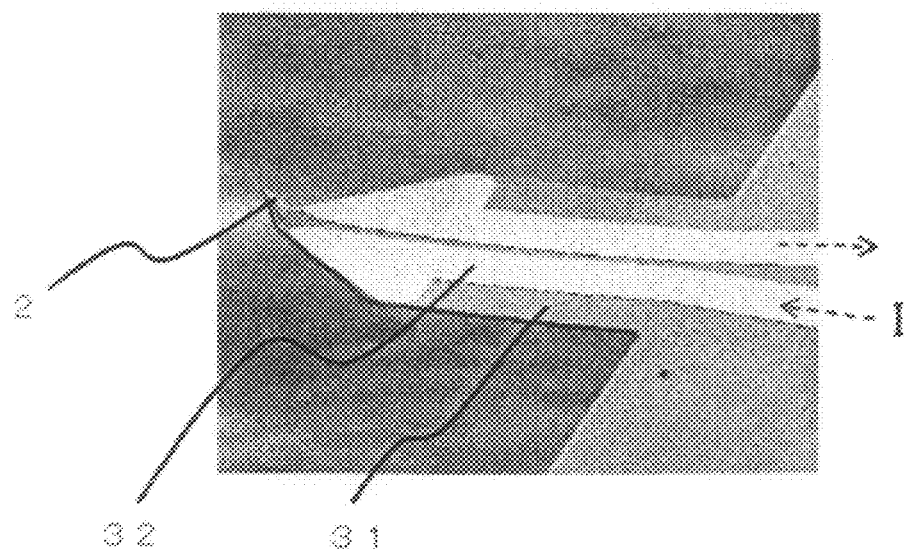
FIG. 3 shows an example of a cantilever that is a type in which a heat generating portion is a metal thin film pattern.

In FIG. 3, a metal thin film pattern 32 is evaporated on the cantilever arm portion 31. The metal thin film pattern has a large width and small resistance at the cantilever arm portion so as to generate little heat. As being close to the tip of the probe 2, the metal thin film pattern becomes thin in width and large in resistance so as to generate heat easily. Therefore, the tip of the probe 2 is heated. Two examples of the cantilever having the heat generating portion are described above, but other methods than the heat generation by the doped resistor or the metal thin film resistor may be used as long as the cantilever has the heat generating portion. Next, a concept of measuring a softening point is described with reference to FIGS. 4A to 4C.

Figure 4A:
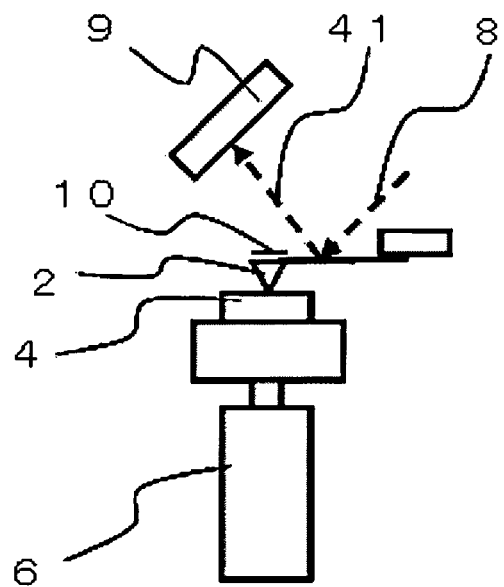
FIGS. 4A to 4C are diagrams of a procedure of measuring a softening point such as glass transition or melting point.
Figure 4B:
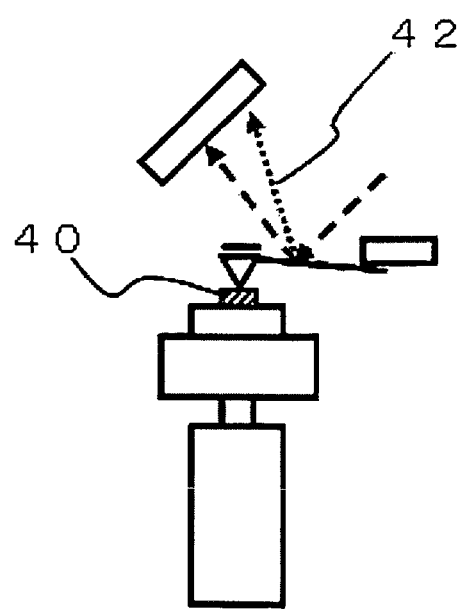
Figure 4C:
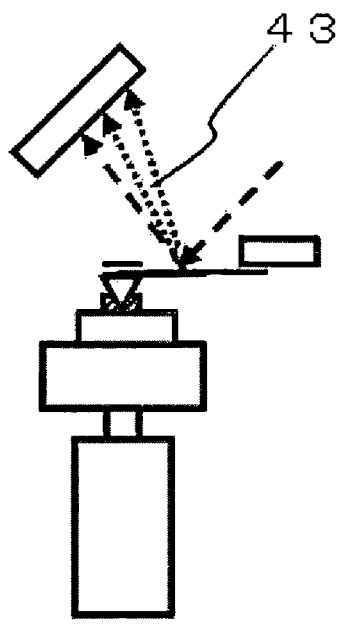

As illustrated in FIG. 4A, in the state where the probe 2 is brought into contact with the sample 4, a position of the reflected light of the laser 8 is detected by the displacement detection unit 9 so as to recognize a position 41 of the reflected light. In FIG. 4B, the heat generating portion 10 heats the probe 2. Then, the sample 4 is heated by the probe 2, and thermal expansion 40 occurs so that the reflected light is shifted to a position 42. This is a state where the sample lifts the probe upward by thermal expansion. In FIG. 4C, when the heating temperature is further increased, the sample 4 reaches the softening point such as glass transition or melting point so as to be softened. Then, the probe 2 sinks in the sample 4 so that the reflected light is shifted to a position 43. In other words, when the heating temperature is increased, the probe is moved upward gradually while the sample is being expanded thermally until just before the softening point when the displacement becomes the largest. Then, the probe is moved downward rapidly when the sample reaches the softening point. Next, a result of automatic measurement of the curve until reaching the softening point as described above with reference to FIGS. 4A to 4C is described with reference to FIG. 5 and subsequent diagrams. It is the result when polyethylene terephthalate (PET) having a melting point of 235° C. is used as the sample.

Figure 5:
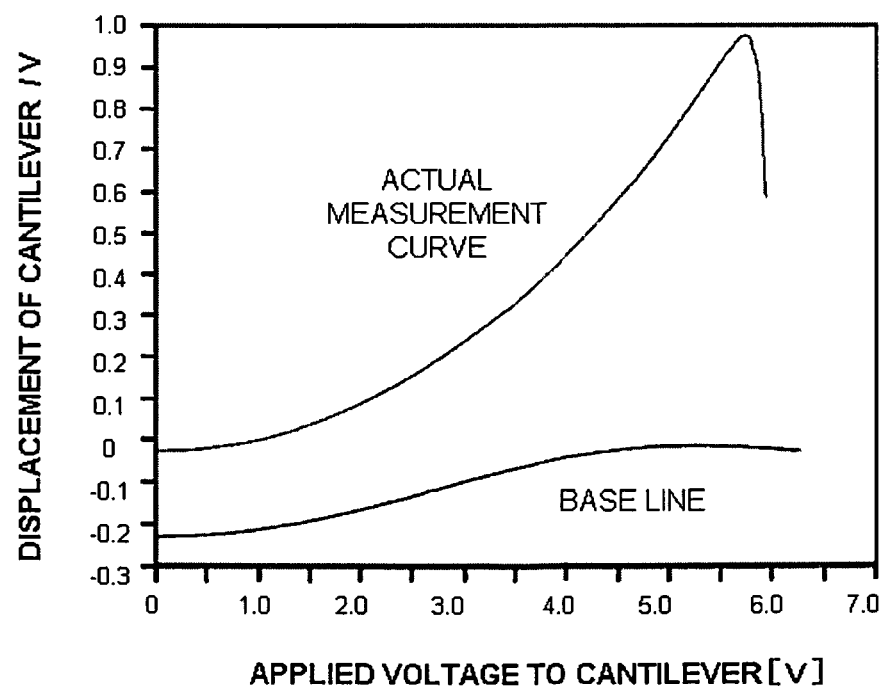
FIG. 5 illustrates a result of actual measurement of a softening curve in the atmosphere.
Figure 6A:
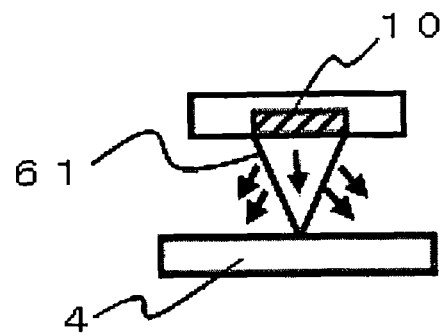
FIGS. 6A to 6C are explanatory diagrams of thermal flow between a probe and a sample in the atmosphere, and FIGS.
Figure 6B:
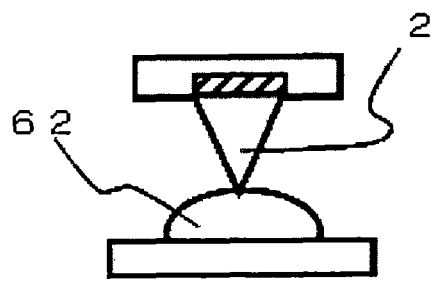
Figure 6C:
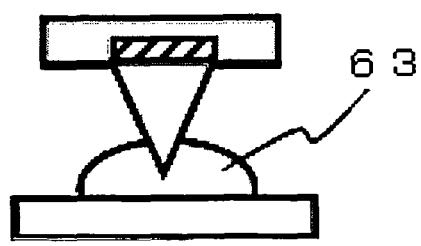

FIG. 5 illustrates an example of an actual measurement curve in the atmosphere, and FIGS. 6A to 6C are schematic diagrams in the atmosphere.

In FIG. 5, the horizontal axis represents a voltage applied to the heat generating portion of the cantilever, and there is a relationship that the heating temperature becomes high as the voltage increases. For instance, if 6 V is applied, the probe is heated up to 235° C. In addition, the vertical axis represents displacement amount of the probe in the vertical direction. The actual measurement curve is plotted in the state where the probe is brought into contact with the sample surface so as to heat the same. In addition, a base line indicates a characteristic such as warpage due to heat of the cantilever itself when the cantilever is heated in a state where the probe is not brought into contact with the sample surface, which is implicated in a base line (origin).

In FIG. 6A, the probe 2 is brought into contact with the sample 4, and heating of the heat generating portion 10 is started. Then, the probe 2 is heated, and heat is transferred from the probe 2 to the sample 4 via the contacting portion between the probe and the sample. Here, because the probe 2 has a pyramidal shape, heat is also transferred from the side surface 61 of the probe 2 to the sample 4 through the air. In FIG. 6B, not only the probe contacting portion of the sample but also a periphery of the contacting portion receives the thermal flow, and hence the thermal expansion 62 of the sample affects also the periphery of the probe contacting portion. This state corresponds to the curved portion increasing upward rapidly in the actual measurement curve illustrated in FIG. 5. In FIG. 6C, when the sample is heated up to a temperature reaching the softening point 63, the probe 2 sinks in the sample so that the curve drops rapidly. The difference obtained by subtracting the base line from the actual measurement curve corresponds to the expansion of the sample affected by the heat.

In contrast to the above-mentioned situation, effectiveness of the present invention embodied in the vacuum is described.

FIG. 7 illustrates an example of an actual measurement curve in the vacuum, and FIG. 8 is a schematic diagram in the vacuum.

The actual measurement curve illustrated in FIG. 7 is apparently different from that of FIG. 5. In the example in the atmosphere illustrated in FIG. 5, the actual measurement curve rises rapidly with respect to the base line, and it is understood that thermal influence to the sample is large and the thermal expansion is large. In contrast, in the example in the vacuum illustrated in FIG. 7, the actual measurement curve varies in parallel with the base line and the probe sinks when the temperature reaches the softening point, which is a reasonable behavior.

As illustrated in FIG. 8A, in the vacuum, the heat generating portion 10 is heated, and the probe 2 is also heated. However, there is no thermal dissipation from the side surface of the probe 2, which is an ideal state. The thermal transfer from the probe 2 to the sample 4 is performed only at the probe contacting portion. Therefore, as illustrated in FIG. 8B, the heat is applied to only the part directly below the contacting portion of the probe 2, and hence only the part is expanded thermally. It is found that the part is definitely small compared with the case in the atmosphere. In FIG. 8C, the temperature reaches the softening point 82. In addition, as recognized from the actual measurement curve, the actual measurement curve varies in parallel with the base line. Because the heat flows in only the part directly below the probe contacting portion, and only the contacting portion is expanded thermally, the softening point is reached straightly in parallel. It is understood that, in the vacuum, the thermal transfer is performed only at the probe contacting portion, and hence local thermal measurement may be performed. Next, an example of actual measurement about how close the measurement points maybe provided when a plurality of measurements are performed is described with reference to the drawing.

FIGS. 9A to 9D illustrate examples of measurement in which 3×3 measurement points are measured while varying the pitch in the atmosphere. As illustrated in FIG. 9A, softening points of nine points (3×3) arranged at 5 μm pitch were measured. As the sample, polyethylene terephthalate (PET) having a melting point of 235° C. was used in the same manner. As illustrated in FIG. 9B, nine softening curves are identical. In other words, thermal history is given to the periphery of the contacting portion by the just previous heating, but if the points are separated by 5 μm, the softening curves are the same as the curve on the sample surface that is not affected by the thermal history. Next, in FIG. 9C, softening points of nine points (3×3) arranged at 1.5 μm pitch were measured. As illustrated in FIG. 9D, nine softening curves are not identical. In other words, the measurement points are too close to each other, and hence thermal history is given to the sample in the previous heating operation. Therefore, it is interpreted that the softening curve becomes the curve of the sample surface that is affected by the thermal history despite of the same heating operation. Next, as a noted point of the present invention, an example of the case in the vacuum is described.

As illustrated in FIG. 10A, softening points of nine points (3×3) arranged at 0.5 μm pitch were measured. As illustrated in FIG. 10B, nine softening curves are identical. It is understood that the periphery of the contacting portion of the sample is hardly affected by heat in the vacuum. At the same time, local heating or local thermal measurement may be performed with high resolution in the planar direction. Next, a degree of vacuum is described.

As illustrated in FIG. 6A, the heat dissipates from the side surface 61 of the probe 2 through the air in the atmosphere and reaches the sample surface. In the vacuum environment, as illustrated in FIG. 8A, the thermal dissipation from the side surface 61 of the probe 2 may be eliminated, and hence the thermal influence to the sample surface may be suppressed. The thermal dissipation from the side surface 61 of the probe 2 depends on concentration of air. In the present invention, the vacuum state is set to 1/100 atmospheric pressure ($10^3$ Pa). The thermal dissipation from the side surface of the probe may be lower than 1% under the corresponding degree of vacuum. Thermal transfer between the probe and the sample contacting portion becomes 99%, and hence the probe contacting portion becomes dominant.

[Embodiment 2]

Embodiment 2 of the present invention is described with reference to the drawings. FIG. 11 illustrates a general structure of a thermal conductivity measuring apparatus using a scanning probe microscope. A description overlapping with that in Embodiment 1 is omitted. In FIG. 11, in addition to the voltage applying unit 16, a current detection unit 17 is provided. When a voltage is applied to the heat generating portion of the cantilever, a current may be detected at the same time. By detecting the current, a resistance variation of the heat generating portion 10 may be detected, and also a temperature variation of the heat generating portion may be detected. A constant voltage is applied to the heat generating portion 10 of the cantilever 1, and the probe is heated and is brought into contact with the sample so that the sample surface is scanned. Then, in accordance with thermal conduction distribution of the sample surface, quantity of heat that is transferred to the sample varies. The variation of the heat quantity causes the resistance variation of the heat generating portion, and which causes temperature variation, which becomes a quantity varying in accordance with the thermal conduction. The cantilever that is used in the thermal conduction measurement may be the type illustrated in FIG. 2 and FIG. 3. A resistance of the doped resistor illustrated in FIG. 2 varies in accordance with temperature, and a resistance of the metal thin film pattern illustrated in FIG. 3 also varies in accordance with temperature. If the resistance variation of the heat generating portion has dependency on temperature, the cantilever having the heat generating portion may be any type.

Also in the thermal conduction measurement, effectiveness of the present invention in the vacuum has become apparent. The effectiveness in the vacuum is described with reference to FIGS. 12A to 12E. FIG. 12A shows a result that a resistance of the heat generating portion of the cantilever varies in accordance with a distance between the probe and the sample, i.e., is affected by heat. A constant voltage is applied to the heat generating portion of the cantilever so as to be in the heated state. The resistance value in accordance with the temperature at that time is detected. Next, when the cantilever is moved to be close to the sample surface and causes heat transfer with the sample surface, temperature of the heat generating portion of the cantilever is decreased so that a resistance thereof varies. In the atmosphere, if being apart from the sample surface by 300 μm, no heat transfers to the sample surface, and hence the resistance does not vary. However, as being 200 μm or closer, the resistance is decreased gradually and continuously. In other words, temperature of the heat generating portion is being decreased. It is found that the thermal transfer to the sample is performed via the air in accordance with the distance between the sample and the probe. In contrast, when the probe and the sample are moved to be close to each other similarly in the vacuum, there is no dependency on the distance. Only when the probe is brought into contact with the sample, the resistance varies so that the temperature is decreased.

FIG. 12B illustrates the case in the atmosphere, where the heat generating portion of the cantilever is the doped resistor type. If the probe approaches the sample surface in the state where heat is dissipating from the probe tip and the side surface via the air, the heat transfer amount varies. FIG. 12C illustrates the case in the vacuum, where no thermal dissipation via the air occurs. Therefore, the resistance variation appears in the curve only when contact occurs.

FIG. 12D illustrates the case in the atmosphere, where the heat generating portion of the cantilever is the metal thin film pattern type. If the probe approaches the sample surface in the state where heat is dissipating from the probe tip and the side surface via the air, the heat transfer amount varies. FIG. 12E illustrates the case in the vacuum, where no thermal dissipation via the air occurs. Therefore, the resistance variation appears in the curve only when contact occurs.

Next, an example of measuring a thermal conduction image of an uneven sample is described.

FIGS. 13A to 13C show an example of measuring a surface shape image and a thermal conduction image in the atmosphere. FIG. 13A shows the surface shape image of the sample in which a dark portion 131 (square portion) has a low height like a recess, while a bright portion 132 has a high height like a protrusion. The bright portion and the dark portion in the surface shape image are made of the same material. FIG. 13B shows the thermal conduction image. In the thermal conduction image, if the portions are made of the same material, the portions are expected to be represented by the same color, but dark and bright portions are distinguished in accordance with the shapes. The reason is considered with reference to FIG. 13C. When the heat generating portion 10 is heated, the probe 2 is heated, and the heat dissipates from the tip 122 and the side surface 121 via the air. When the probe 2 scans a bottom surface 124, because the heat generating portion 10 is close to an upper surface 123, the thermal dissipation from the side surface 121 increases so that temperature of the heat generating portion 10 is decreased. Therefore, it is measured incorrectly that the bottom surface 124 has good thermal conduction. Next, when the probe 2 scans the upper surface 123, because the heat generating portion 10 is apart from the upper surface 123, the thermal dissipation from the side surface 121 is decreased so that the temperature of the heat generating portion 10 is increased compared with the case of scanning the bottom surface 124. Therefore, it is measured incorrectly that the upper surface 123 has bad thermal conduction. Despite the upper surface 123 and the bottom surface 124 are made of the same material, the signal of the thermal conduction contains height information in a mixed manner.

FIGS. 14A to 14C show an example of measuring the surface shape image and the thermal conduction image in the vacuum. FIG. 14A shows the surface shape image of the sample in which the dark portion 131 (square portion) has a low height like a recess, while the bright portion 132 has a high height like a protrusion. The bright portion and the dark portion in the surface shape image are made of the same material. FIG. 14B shows the thermal conduction image. In the thermal conduction image, because the portions are made of the same material, the portions are represented by the same color. When the measurement is performed in the vacuum, the thermal conduction image is measured correctly. The reason is considered with reference to FIG. 14C. When the heat generating portion 10 is heated, the probe 2 is heated, but there is no thermal dissipation from the side surface 121 of the probe because there is no air. Only the thermal conduction from the tip 122 to the sample 4 occurs. Both in scanning the bottom surface 124 by the probe 2 and in scanning the upper surface 123 by the same, thermal transfer to the sample 4 occurs only from the tip 122. Therefore, because the bottom surface 124 and the upper surface 123 are made of the same material and have the same thermal conduction characteristic, they have the same thermal conduction in the thermal conduction image, which means that the measurement is performed correctly. Next, an actual measurement example of the cantilever in which the heat generating portion is the metal thin film pattern type is described.

FIGS. 15A to 15C show an example of measuring a surface shape image and a thermal conduction image in the atmosphere. FIG. 15A shows the surface shape image of the sample in which the dark portion 131 (square portion) has a low height like a recess, while the bright portion 132 has a high height like a protrusion. The bright portion and the dark portion in the surface shape image are made of the same material. FIG. 15B shows the thermal conduction image. In the thermal conduction image, if the portions are made of the same material, the portions are expected to be represented by the same color, but dark and bright portions are distinguished in accordance with the shapes. The reason is considered with reference to FIG. 15C. When the heat generating portion 10 is heated, the probe 2 is heated, and the heat dissipates from the tip 122 and the side surface 121 via the air. When the probe 2 scans the bottom surface 124, because the heat generating portion 10 is close to the upper surface 123, the thermal dissipation from the side surface 121 increases so that temperature of the heat generating portion 10 is decreased. Therefore, it is measured incorrectly that the bottom surface 124 has good thermal conduction. Next, when the probe 2 scans the upper surface 123, because the heat generating portion 10 is apart from the upper surface 123, the thermal dissipation from the side surface 121 is decreased so that the temperature of the heat generating portion 10 is increased compared with the case of scanning the bottom surface 124. Therefore, it is measured incorrectly that the upper surface 123 has bad thermal conduction. Despite the upper surface 123 and the bottom surface 124 are made of the same material, the signal of the thermal conduction contains height information in a mixed manner.

FIGS. 16A to 16C show an example of measuring the surface shape image and the thermal conduction image in the vacuum. FIG. 16A shows the surface shape image of the sample in which the dark portion 131 (square portion) has a low height like a recess, while the bright portion 132 has a high height like a protrusion. The bright portion and the dark portion in the surface shape image are made of the same material. FIG. 16B shows the thermal conduction image. In the thermal conduction image, because the portions are made of the same material, the portions are represented by the same color. When the measurement is performed in the vacuum, the thermal conduction image is measured correctly. The reason is considered with reference to FIG. 16C. When the heat generating portion 10 is heated, the probe 2 is heated, but there is no thermal dissipation from the side surface 121 of the probe because there is no air. Only the thermal conduction from the tip 122 to the sample 4 occurs. Both in scanning the bottom surface 124 by the probe 2 and in scanning the upper surface 123 by the same, thermal transfer to the sample 4 occurs only from the tip 122. Therefore, because the bottom surface 124 and the upper surface 123 are made of the same material and have the same thermal conduction characteristic, they have the same thermal conduction in the thermal conduction image, which means that the measurement is performed correctly. Next, a degree of vacuum is described.

As illustrated in FIG. 13C, the heat dissipates from the side surface 121 of the probe 2 through the air in the atmosphere and reaches the sample surface. In the vacuum environment, as illustrated in FIG. 14C, the thermal dissipation from the side surface 121 of the probe 2 maybe eliminated, and hence the thermal influence to the sample surface may be suppressed. The thermal dissipation from the side surface 61 of the probe 2 depends on concentration of air. In the present invention, the vacuum state is set to 1/100 atmospheric pressure ($10^3$ Pa). The thermal dissipation from the side surface of the probe may be lower than 1% under the corresponding degree of vacuum. Therefore, thermal transfer between the probe and the sample contacting portion becomes 99%, and hence the probe contacting portion becomes dominant.

In addition, in the measurement in the atmosphere, it is found that if the sample has an uneven surface, there is a defect that the thermal conduction image contains height information of the unevenness despite the portions are made of the same material when the cantilever with the heat generating portion scans the sample. In contrast, in the measurement in the vacuum, the thermal exchange occurs only at the contacting portion between the probe tip and the sample. Therefore, the thermal conduction image may be measured accurately.

[Embodiment 3]

The above-mentioned embodiments describe the method of performing the softening point measurement and the thermal conduction measurement in the vacuum, so that air is rarefied in the space at the periphery of the probe and the sample surface for eliminating the thermal conduction via the air. Because the thermal exchange is performed only at the probe contacting portion, the thermal dissipation from the side surface of the probe may be eliminated.

On the other hand, in order to reduce the thermal dissipation from the side surface of the probe as described above, as another example besides the vacuum, Embodiment 3 of the present invention is described with reference to the drawings. FIGS. 17A and 17B illustrate an example of thermal insulation coating for suppressing the thermal dissipation from the side surface of the probe. FIG. 17A illustrates a state before the thermal insulation coating. The probe 2 is made of silicon material, for example, and the side surface of the probe is usually covered with a natural oxide film 171 ($SiO_2$) having a thickness of approximately 2.4 nm. When the heat generating portion 10 heats the probe 2, thermal dissipation 172 occurs from the probe to the side surface of the probe and further to the air via the natural oxide film. In this case, thermal conduction ratio of the natural oxide film 171 works as thermal resistance, and hence thermal dissipation amount to the air is determined. FIG. 17B illustrates a state where the thermal insulation coating 173 is formed on the side surface of the probe while the probe tip is not coated. For instance, if an $SiO_2$ coat having a thickness of approximately 240 nm is formed utilizing a semiconductor process, a thermal resistance of thermal insulation coating increases by 100 times compared with the thickness of the natural oxide film before the coating. Therefore, heat is hardly transferred, and hence the thermal dissipation amount to the air may be suppressed. It is supposed that the thermal dissipation amount to the air is "100" before coating, with the thermal conduction corresponding to a natural oxide film having a thickness of 2.4 nm. If the thermal insulation coating of the same material of $SiO_2$ having a thickness of 240 nm is formed, the thermal dissipation amount to the air becomes $100 \times 1/100 = 1$ because the thermal resistance is proportional to the thickness in the same material. In addition, because the probe tip is not covered with the thermal insulation coating, the thermal exchange may be performed only at the probe contacting portion.

If the softening point measurement described above in Embodiment 1 is performed by using the cantilever with the thermal insulation coating instead of using the vacuum, the same advantage is obtained in that the thermal history is not given to the periphery of the probe contacting portion. In addition, if the thermal conduction measurement described above in Embodiment 2 is performed, it is possible to perform the thermal conduction measurement that is not affected by height, for example, by unevenness of the sample.

In the present invention, a resistance against thermal transfer of the side surface of the probe is increased by the thermal insulation coating. By increasing the resistance against the thermal conduction by 100 times, the amount of the thermal dissipation to the air is reduced to $1/100$ or less. Thus, the thermal dissipation from the side surface of the probe may be lower than 1% of that before thermal insulation coating. The thermal exchange between the probe and the sample contacting portion becomes 99%, so that the probe contacting portion becomes dominant both in the softening point measurement and in the thermal conduction measurement.

In this embodiment, it is described that the thermal insulation coating is formed on the side surface of the probe instead of using the vacuum, so that the heat dissipation from the side surface of the probe may be suppressed while the heat exchange may be performed only at the probe contacting portion. Thus, the same effect as in the case of increasing the degree of vacuum may be obtained.

Hereinafter, the description is continued in the embodiment of improving the degree of vacuum.

[Embodiment 4]

As Embodiment 4, concerning the thermal conduction measurement of the thin film, an influence of adsorbed water on the conventional sample surface in the atmosphere and an effect of the measurement in the vacuum environment according to the present invention are described.

FIGS. 18A to 18C illustrate a real example of measuring a surface shape and a thermal conduction image of a sample in the atmosphere, in which LB films exist like islands on a silicon substrate. FIG. 18A illustrates the surface shape image in which a dark portion is a silicon substrate 181, and a bright portion is a LB film 182. The LB film is a super thin film having a thickness of 1 to 2 nm. In FIG. 18B as the thermal conduction image, a difference of color (a difference of thermal conduction property) is detected between the silicon substrate and the LB film. This result shows that the LB film is displayed brighter than the surface of the silicon substrate, so that the surface of the silicon substrate has better thermal conduction.

In contrast, in the measurement according to the present invention in the vacuum ($1/100$ atmospheric pressure ($10^3$ Pa) or lower), a different result is shown as illustrated in FIG. 19A to 19C. Specifically, the surface shape image has no difference of brightness between the silicon substrate 181 and the LB film 182 as illustrated in FIG. 19A, but the thermal conduction image has a difference of brightness as illustrated in FIG. 19B. This may be described as follows.

As illustrated in FIG. 18C, the silicon substrate 181 has an affinity for water in the atmosphere and is covered with adsorbed water 183. In contrast, the LB film 182 is hydrophobic and there is no adsorbed water. This adsorbed water causes thermal dissipation 184 in the surface direction when the probe 2 contacts with the adsorbed water 183 on the silicon substrate 181, so that temperature of the heat generating portion 10 is decreased. On the other hand, when the probe 2 moved onto the LB film 182, the thermal dissipation 184 via the adsorbed water is eliminated, so that temperature of the heat generating portion 10 is increased. As a result, in the atmosphere, the silicon substrate 181 has better thermal conduction than the LB film 182.

However, in the vacuum environment, as illustrated in FIG. 19C, the adsorbed water on the silicon substrate 181 is eliminated. Therefore, in the measurement by the probe 2 on the silicon substrate 181, there is no thermal diffusion, so-called thermal dissipation to the adsorbed water, and the thermal conduction image is obtained based on the true thermal conduction of the surface of the silicon substrate. In contrast, in relative comparison with the thermal conduction image of the surface of the LB film 182 in the same environment, the result is different from that in the atmosphere.

Therefore, conventionally, between materials to be compared having similar heat quantity, under the characteristic concerning affinity or hydrophobic property of the material surface, in the thermal conduction measurement of a super thin film having a thickness of approximately 1 to 2 nm in which thermal conduction via the adsorbed water on the surface is dominant, there is a case where the order of thermal conduction is reversed between the materials to be compared. In the present invention, it is found that correct thermal conduction may be measured by setting a predetermined degree of the vacuum so that the adsorbed water on the surface is evaporated, and by preventing the thermal dissipation from the side surface of the probe via the air so that the probe is brought into contact with the original surface of the sample surface.

[Embodiment 5]

It is found that the probe and the sample exchange heat only at the contacting portion in the vacuum. FIG. 20 illustrates an embodiment of measuring the thermal conduction by changing temperature of the sample. Instead of the sample table 5 in FIG. 11, a heating and cooling table 201 is disposed on the sample moving unit 6. The heating and cooling table 201 includes a heater and a temperature sensor inside and is heated up to a desired temperature. In addition, the heating and cooling table 201 is cooled by a cooling unit (not shown) and thermal conduction and may be controlled to be any temperature including negative temperature by cooling and heating. On the heating and cooling table 201, a substrate 202 having a thin film 203 is disposed, and the substrate 202 is controlled to be any temperature by the heating and cooling table 201. For instance, it is supposed that the heating and cooling table is heated up to 100° C. Next, a constant voltage is applied to the heat generating portion 10 of the cantilever so as to be heated up to 50° C., for example. The heat generating portion 10 has a resistance corresponding to the heating temperature.

First, if the probe 2 is brought into direct contact with the upper surface of the heating and cooling table 201, heat transfers only from the probe contacting portion to the probe 2 because the heating and cooling table 201 is at 100° C. while the heat generating portion 10 is at 50° C. Then, the temperature of the heat generating portion 10 is increased, and the temperature of the heat generating portion is also increased, so that the resistance of the heat generating portion is increased. As described above, temperature of the heat generating portion may be measured from variation of the resistance. A temperature rise of the heat generating portion is denoted by A. Next, the probe 2 is brought into contact with the substrate 202, and a temperature rise of the heat generating portion 10 may be measured similarly as B. Further, the probe 2 is brought into contact with the thin film 203, and a temperature rise of the heat generating portion 10 may be measured as C in the same manner. From a difference between B and A, a thermal conduction ratio of the substrate 202 itself may be measured. In addition, from a difference between C and B, a thermal conduction ratio of the thin film 203 itself may be measured. If the temperature rise is small, the thermal transfer amount is small because the thermal conduction is low. On the contrary, if the temperature rise is large, the thermal transfer amount is large because the thermal conduction is high. In this way, a thermal conduction degree may be measured. Concerning heat from the heating and cooling table, in the vacuum, thermal conduction via the air is eliminated and heat transfers only from the contacting portion of the probe 2 to the probe 2 and the heat generating portion 10. Therefore, thermal conduction characteristic of only the contacting portion may be measured.

In addition, if the temperature of the heating and cooling table 201 is set to a high temperature like 500° C., thermal conduction of a thin film at high temperature may be measured. In addition, if the heating and cooling table is cooled to −100° C., for example, thermal conduction of a thin film in a cooled state may be measured. It is possible to measure dependency of thermal conduction of a thin film on temperature correctly.

Note that it is possible to combine the cantilever including the thermal insulation coating 173 on the side surface of the probe described in Embodiment 3 and the heating and cooling table 201 in the atmosphere instead of using the vacuum. Heat from the heating and cooling table hardly transfer because of the thermal insulation coating, heat may be exchanged only at the probe contacting portion, so that the same effect may be obtained as in the case of using the vacuum.

In addition, it is desirable to use the vacuum so that the adsorbed water on the sample surface is evaporated for measuring the original thermal conduction characteristic of the sample surface, but it is possible to adopt the following method in the atmosphere. The sample is heated by the heating and cooling table 201 up to 100° C. or higher, for example, and the cantilever described in Embodiment 3 may be used, which includes the thermal insulation coating 173 formed on the side surface of the probe. Heat from the heating and cooling table hardly transfer because of the thermal insulation coating on the side surface of the probe, so that heat may be exchanged only at the probe contacting portion. In addition, the adsorbed water on the sample surface is evaporated when being heated up to 100° C. or higher. Therefore, even in the atmosphere, thermal conduction may be measured without influence of the adsorbed water.

What is claimed is:

1. A softening point measuring apparatus using a probe microscope as a base,
the softening point measuring apparatus comprising:
a cantilever including a probe at a tip thereof and a heat generating portion at a vicinity of the probe;
a voltage applying unit for applying a voltage to the heat generating portion;
a displacement detection unit for detecting a displacement of the cantilever;
a sample moving unit for moving a sample;
a vacuum chamber in which the probe and the sample are disposed; and
a vacuum pumping unit for the vacuum chamber, wherein:
the heat generating portion is heated for heating the probe so as to heat a contacting portion with the sample locally for detecting a flection amount of the cantilever so as to measure a softening point of the sample; and
an ambient environment of the probe and the sample is $1/100$ atmospheric pressure ($10^3$ Pa) or lower.

2. A softening point measuring apparatus using a probe microscope as a base,
the softening point measuring apparatus comprising:
a cantilever including a probe at a tip thereof and a heat generating portion at a vicinity of the probe;
a voltage applying unit for applying a voltage to the heat generating portion;
a displacement detection unit for detecting a displacement of the cantilever;
a sample moving unit for moving a sample; and
a chamber in which the probe and the sample are disposed, wherein:
the heat generating portion is heated for heating the probe so as to heat a contacting portion with the sample locally for detecting a flection amount of the cantilever so as to measure a softening point of the sample; and
the probe includes a thermal insulation material provided so as to cover a side surface thereof, to thereby reduce thermal dissipation from the side surface of the probe to $1/100$ or less in heat quantity compared with a case where the thermal insulation material is not provided.

3. A softening point measuring apparatus according to claim 2, wherein the thermal insulation material has a thickness of at least approximately 100 times a thickness of a natural oxide film that is formed on the side surface of the probe in atmosphere.

4. A softening point measuring apparatus according to claim 3, wherein the thermal insulation material comprises a film made of SiO$_2$, having a thickness of at least approximately 240 nm coating the probe.

5. A thermal conductivity measuring apparatus using a probe microscope for measuring thermal conduction of a sample as a base, the thermal conductivity measuring apparatus comprising:
a cantilever including a probe at a tip thereof and a heat generating portion at a vicinity of the probe;
a voltage applying unit for applying a voltage to the heat generating portion;
a displacement detection unit for detecting a displacement of the cantilever;
a sample moving unit for moving the sample;
a vacuum chamber in which the probe and the sample are disposed; and
a vacuum pumping unit for the vacuum chamber, wherein:
the thermal conductivity measuring apparatus performs measuring of the thermal conduction of a surface of the sample via a contacting portion between the sample and the probe by measuring a resistance variation in the heat generating portion and detecting a temperature variation of the cantilever as a variation of a resistance value; and
an ambient environment of the probe and the sample is $\frac{1}{100}$ atmospheric pressure ($10^3$ Pa) or lower.

6. A thermal conductivity measuring apparatus according to claim 5, further comprising a heating and cooling unit for the sample.

7. A thermal conductivity measuring apparatus using a probe microscope as a base, the thermal conductivity measuring apparatus comprising:
a cantilever including a probe at a tip thereof and a heat generating portion at a vicinity of the probe;
a voltage applying unit for applying a voltage to the heat generating portion;
a displacement detection unit for detecting a displacement of the cantilever;
a sample moving unit for moving a sample; and
a chamber in which the probe and the sample are disposed, wherein:
the thermal conductivity measuring apparatus performs measuring of thermal conduction of a surface of, the sample via a contacting portion between the sample and the probe by measuring a resistance variation in the heat generating portion and detecting a temperature variation of the cantilever as a variation of a resistance value; and
the probe includes a thermal insulation material provided so as to cover a side surface thereof, to thereby reduce thermal dissipation from the side surface of the probe to $\frac{1}{100}$ or less in heat quantity compared with a case where the thermal insulation material is not provided.

8. A thermal conductivity measuring apparatus according to claim 7, further comprising a heating and cooling unit for the sample.

9. A thermal conductivity measuring apparatus according to claim 7, wherein the thermal insulation material has a thickness of at least approximately 100 times a thickness of a natural oxide film that is formed on the side surface of the probe in atmosphere.

10. A thermal conductivity measuring apparatus according to claim 9, further comprising a heating and cooling unit for the sample.

11. A thermal conductivity measuring apparatus according to claim 9, wherein the thermal insulation material comprises a film made of SiO$_2$, having a thickness of at least approximately 240 nm coating the probe.

12. A thermal conductivity measuring apparatus according to claim 11, further comprising a heating and cooling unit for the sample.

* * * * *